United States Patent [19]

Tanaka et al.

[11] Patent Number: 4,500,441
[45] Date of Patent: Feb. 19, 1985

[54] CONTACT LENS CLEANING AND STORAGE COMPOSITION

[75] Inventors: Kyoichi Tanaka; Akira Tsuzuki, both of Nagoya; Shunichi Hioki, Ichinomiya, all of Japan

[73] Assignee: Toyo Contact Lens Co., Ltd., Japan

[21] Appl. No.: 586,883

[22] Filed: Mar. 9, 1984

Related U.S. Application Data

[63] Continuation of Ser. No. 375,095, May 5, 1982, abandoned.

[30] Foreign Application Priority Data

May 13, 1981 [JP] Japan ................... 56-70766

[51] Int. Cl.$^3$ ................................. C11D 3/48
[52] U.S. Cl. ................. 252/89.1; 252/106; 252/173; 252/174.21; 252/541; 252/549; 252/551; 252/559; 252/DIG. 1; 252/DIG. 10; 252/DIG. 14
[58] Field of Search ........... 252/DIG. 1, DIG. 14, 252/173, DIG. 10, 174.21, 559, 549, 541, 551, 106, 89.1; 424/78, 80

[56] References Cited

U.S. PATENT DOCUMENTS

| | | | |
|---|---|---|---|
| 3,884,826 | 5/1975 | Phares, Jr. et al. | 252/106 |
| 4,224,195 | 9/1980 | Kawasaki et al. | 252/551 |
| 4,244,840 | 1/1981 | Straw | 252/551 |
| 4,259,202 | 3/1981 | Tanaka et al. | 252/107 |
| 4,284,534 | 8/1981 | Ehrlich | 252/DIG. 14 |
| 4,306,997 | 12/1981 | Oneto et al. | 252/551 |

FOREIGN PATENT DOCUMENTS

| | | |
|---|---|---|
| 2341785 | 2/1975 | Fed. Rep. of Germany . |
| 2840464 | 4/1980 | Fed. Rep. of Germany . |
| 60-92999 | 7/1981 | Japan . |
| 1040543 | 9/1966 | United Kingdom . |

Primary Examiner—Paul Lieberman
Attorney, Agent, or Firm—Armstrong, Nikaido, Marmelstein & Kubovcik

[57] ABSTRACT

A cleaning and storage composition for contact lens comprising an anionic surface active agent and a non-ionic surface active agent. The composition has synergistically increased cleaning effect and safety to eye tissue by the combination use of anionic and non-ionic surface active agents, and it is suitable for use in storing contact lenses as well as cleaning the lenses.

4 Claims, No Drawings

CONTACT LENS CLEANING AND STORAGE COMPOSITION

This application is a continuation of application Ser. No. 375,095, filed May 5, 1982 now abandoned.

BACKGROUND OF THE INVENTION

The present invention relates to a contact lens cleaning and storage composition which is suitable for storing a contact lens as well as cleaning it.

Various contact lenses have hitherto been employed, and they are classified roughly into a water-absorptive contact lens and a water-nonabsorptive contact lens. Representative water-nonabsorptive contact lenses are polymethyl methacrylate contact lenses and silicone rubber contact lenses. Further, in recent years, contact lenses made of cellulose acetate butyrate and contact lenses made of a copolymer of a polysiloxanyl alkyl methacrylate and methyl methacrylate or the like are known as water-nonabsorptive contact lenses having an oxygen permeability. These contact lenses, particularly water-nonabsorptive contact lenses, are contaminated when worn on the eyes, by sticking of secretions in the eyes such as proteins and lipids to the lens surface. For this reason, the contact lenses taken off from the eyes must be promptly cleaned to remove contaminants such as proteins and lipids sticking to the lens surface. Wearing of insufficiently cleaned contact lenses results in a great cause for uncomfortable symptoms such as foggy sight, pain and ocular injection, so the wearing must be stopped.

Cleaning of contact lenses has been conducted generally by a method in which a solution containing an ether of a higher alcohol in a physiological saline water is employed as a cleaning solution and the lenses are washed and rubbed with fingers. The cleaned contact lenses are rinsed with a tap water or a physiological saline solution and then stored by soaking them in a physiological saline solution or the like. The storage of the contact lens in a soaking solution is necessary for water-absorptive contact lenses to maintain them in a hydrated state. Even in case of water-nonabsorptive contact lenses, it is desirable to store them in a soaking solution in maintaining the lens surface hydrophilic and in storing cleanly and sanitarily.

In general, it is necessary to employ separately a cleaning solution and a storing solution for the cleaning and storage of contact lenses. The contact lens cleaning solution is required to have an excellent cleaning ability, since the object of its use is cleaning of contact lenses. The contact lens storing solution is desirable to be high in safety and low in irritation to the eye even in case of using it for water-nonabsorptive contact lenses, to say nothing of water-absorptive contact lenses, in that the contact lenses soaked for storage are taken out from the storing solution and worn on the eyes. The use of separate cleaning and storage solutions is very inconvenient to the user, since it requires troublesome procedures and also there is a case where the user stores the contact lenses in a cleaning solution by mistake.

The object of the present invention is to provide a cleaning and storage composition for contact lenses.

A further object of the invention is to provide a cleaning and storage composition for contact lenses, especially for water-nonabsorptive contact lenses, which has both cleaning and storing functions.

A still further object of the invention is to provide a cleaning and storage solution which is usable as a cleaning solution with a high cleaning ability and is also usable as a storage solution in safety and without giving irritation to the eyes.

SUMMARY OF THE INVENTION

In accordance with the present invention, there is provided a cleaning and storage composition for contact lenses comprising an anionic surface active agent and a non-ionic surface active agent.

The combination use of an anionic surface active agent and a non-ionic surface active agent produces an excellent synergistic effect such that the safety to the eye tissue can be improved as well as the increase of the cleaning ability to contaminants sticking to the lens surface as compared with the use of either anionic or non-ionic surface active agent.

DETAILED DESCRIPTION

The anionic surface active agents used in the present invention include, for instance, sodium alkylbenzene sulfonates, sodium alkyl sulfates, sodium α-olefin sulfonates, sodium polyoxyethylene alkylether sulfates, sodium alkyloylmethyltaurinate, sodium alkyloylsarcosinate, sodium polyoxyethylene alkylether phosphates, sodium di(polyoxyethylene alkylether)phosphates, sodium polyoxyethylene alkylphenylether sulfates, and the like. Particularly, sodium alkylbenzene sulfonates, sodium alkyl sulfates, sodium α-olefin sulfonates, sodium polyoxyethylene alkylether sulfates and sodium polyoxyethylene alkylphenyl sulfates have an excellent cleaning ability, and an effective cleaning effect can be obtained by soaking and storage in a very short period of time when they are employed in combination with non-ionic surface active agents. Alkali metal salts of fatty acids are anionic surface active agents, but are not comprehended in the term "anionic surface active agent" as used herein, since they have a little effect on cleaning against contaminants sticking to the surface of contact lenses. The anionic surface active agents may be employed alone or in admixture thereof.

The non-ionic surface active agents used in the present invention include, for instance, polyoxyethylene higher fatty acid esters, higher fatty acid esters with polyoxyalkylene-polyoxyethylene copolymers, higher fatty acid esters with polyhydric alcohols, higher fatty acid esters with polyoxyethylene polyhydric alcohols such as polyoxyethylene glyceryl fatty acid esters and polyoxyethylene sorbitan fatty acid esters, polyglycerin fatty acid esters, polyoxyethylene alkyl ethers, polyglycerin ethers with alcohols, polyoxyethylene fatty acid amides, polyoxyethylene alkylamines, polyoxyethylene alkylphenyl ethers, condensate of polyoxyethylene alkylphenol ether with formaldehyde, polyoxyethylene-polyoxypropylene block copolymer, phosphates, polyethyleneglycol adduct of hydrogenated castor oil, castor oil or sterol, polyoxyethylene sorbitan fatty acid esters, and the like. The polyglycerin fatty acid esters, polyoxyethylene fatty acid esters, polyoxyethylene alkyl ethers and polyoxyethylene alkylphenyl ether are particularly effective in increasing the cleaning effect. The non-ionic surface active agents may be employed alone or in admixture thereof.

The ratio of the anionic surface active agent to the non-ionic surface active agent is selected from about 32:68 to about 94:6 by weight. In general, the anionic surface active agent has a stronger cleaning ability than the non-ionic surface active agent, and when the proportion of the anionic surface active agent is less than the above range, a sufficient effect on cleaning of contact lenses is not exhibited. On the other hand, in general, the non-ionic surface active agent has a higher safety than the anionic surface active agent, and when the proportion of the non-ionic surface active agent is less than the above range, there are cases where a problem occurs in safety which is important for the contact lens cleaning and storage composition.

Purified water or distilled water is employed as a solvent for preparing the cleaning and storage solution of the invention. It is essential for the present invention to employ the anionic and non-ionic surface active agents in combination. It is desirable that the total concentration of both anionic and non-ionic surface active agents in the cleaning and storage solution falls within the range of about 0.05 to about 4.5%. When the total concentration is less than the above range, a sufficient effect on cleaning contaminants sticking to the contact lens surface cannot be obtained. When the total concentration is more than the above range, there may be cases where the surface active agents remain on contact lenses and they give an irritation to the eye tissue or exert a bad influence upon the lens material.

An aqueous solution containing both anionic and non-ionic surface active agents in the above-mentioned mixing ratio and having a total concentration thereof within the above-mentioned range according to the present invention has excellent effects. That is to say, by the combination use of the anionic and non-ionic surface active agents, the cleaning ability to contaminants on the contact lens surface can be increased and simultaneously the safety to the eye tissue which is essential for contact lens cleaning and storage compositions can also be improved, in comparison with the single use of either anionic or non-ionic surface active agent as in a conventional contact lens cleaning composition.

In addition to the anionic and non-ionic surface active agents used as essential components in the present invention, the cleaning and storage composition of the invention may contain polysaccharides or their derivatives as an auxiliary component for the purpose of increasing the viscosity of the cleaning and storage solution or imparting a dispersing or lubricating aciton to the solution. Examples of the polysaccharides or their derivatives are, for instance, alkali metal salts of alginic acid, alkali metal salts of pectic acid, pectic acid derivatives, dextran, xanthan gum, tragacanth gum, agar, locust bean gum, guar gum, methyl cellulose, alkali metal salts of carboxymethyl cellulose, alkali metal salts of carboxyethyl cellulose, propyl methyl cellulose, hydroxyethyl cellulose, hydroxypropyl cellulose, hydroxypropyl methyl cellulose, alkali metal salts of chondroitin sulfuric acid, and the like. Preferable alkali metal salts are sodium and potassium salts. These polysaccharides and derivatives thereof may be employed alone or in admixture thereof. The acidic polysaccharide salts such as the alginates and the chondroitin sulfates are particularly preferred, since these compounds combine with metal ions such as calcium ion on the contact lens surface so as to remove the ions from the lens surface and also to prevent the ions from sticking to the lens surface.

The amount of the above-mentioned auxiliary agent varies depending on the kind and molecular weight of the polysaccharide or its derivative used. The auxiliary agent is employed usually in concentrations of 0.01 to 10% by weight. When the concentration of the auxiliary agent in the obtained cleaning and storage solution is less than the above range, the viscosity-building, dispersing and lubricating effects are not sufficiently exhibited. Even if the auxiliary agent is employed in concentrations over the above-mentioned range, further effects corresponding to the increase of the concentration are not obtained.

In the present invention, use of a buffer is desirable in stabilizing the pH of the obtained contact lens cleaning and storage solution. Examples of the buffer employed in the present invention are ophthalmology-physiologically acceptable buffers such as combinations of boric acid and its sodium salt; phosphoric acid and its sodium salt; citric acid and its sodium salt; lactic acid and its sodium salt; amino acid (e.g. glycine or glutamic acid) and its sodium salt; malic acid and its sodium salt; and the like. The buffer is employed in concentrations of about 0.01 to about 1 mole/liter, preferably about 0.03 to about 0.15 mole/liter. The use of the buffer is advantageous in that the cleaning and storage composition in the form of an aqueous solution can be stabilized and that it can be maintained at pH 4.8 to 8.5, especially pH 7 to 7.4, which is near the pH value of tears, so as to stabilize the lens contour.

The cleaning and storage composition of the present invention may contain a germicide, e.g. ophthalmology-physiologically acceptable germicides such as thimerosal, chlorohexizine, phenylmercury nitrate, benzalkonium chloride, chlorobutanol and bronopol. Usually the germicide is employed in a concentration of 0.0001 to 0.5% by weight, though the suitable concentration varies depending on the kind of the germicide used.

The contact lens cleaning and storage composition of the present invention may further contain a chelating agent, an agent to make the solution isotonic, a hydrogen bond destroying agent such as urea or guanidine, or a salt capable of exhibiting a salting in effect such as sodium thiocyanate, as occasion demands.

The cleaning and storage composition of the present invention is prepared into an aqueous solution form or a granular form. For instance, the cleaning and storage aqueous solution is prepared by adding both of the anionic and non-ionic surface active agents, and if necessary, with other additives, to purified water or distilled water, dissolving them, adjusting the pH of the obtained solution and filtering the solution. The cleaning and storage granular composition is prepared by finely dividing the respective components, agitating them in purified water to give a slurry, kneading the slurry to which a vehicle is added, if necessary, passing the kneaded mass through a mesh, and drying it with heating under reduced pressure to give granules. The granular composition is dissolved for use in a prescribed amount of water by the user.

The present invention is more specifically described and explained by means of the following Examples, in which all % are by weight unless otherwise noted.

It is to be understood that the present invention is not limited to the Examples and various changes and modifications may be made in the invention without departing from the spirit and scope thereof.

EXAMPLE 1

Eighteen kinds of aqueous solutions containing both anionic and non-ionic surface active agents were prepared by dissolving the surface active agents shown in Table 1 in water, together with aqueous solutions for comparison containing only the corresponding anionic and non-ionic surface active agent in the same concentration as the total concentration of the anionic and non-ionic surface active agents.

TABLE 1

| Run No. | Anionic surface active agent | Concentration (%) | Non-ionic surface active agent | Concentration (%) |
|---|---|---|---|---|
| 1 | Sodium lauryl sulfate | 0.50 | Polyethylene glycol(12) octylphenyl ether | 0.15 |
| 2 | Sodium lauryl sulfate | 0.50 | Polyethylene glycol(15) cetyl ether | 0.15 |
| 3 | Sodium lauryl sulfate | 1.00 | Lauroyldiethanolamide | 1.93 |
| 4 | Sodium lauryl sulfate | 0.30 | Polyglycerin(7) monolaurate | 0.20 |
| 5 | Sodium lauryl sulfate | 1.00 | Glycerin monocaprylate | 0.20 |
| 6 | Sodium lauryl sulfate | 0.50 | Diethylene glycol monohexyl ether | 0.20 |
| 7 | Sodium laurylbenzene sulfonate | 1.00 | Lauryldiethanolamide | 2.10 |
| 8 | Sodium laurylbenzene sulfonate | 1.50 | Glycerin monocaprylate | 0.10 |
| 9 | Sodium laurylmethyltaurate | 0.10 | Condensate of polyethylene glycol(30) nonylphenyl ether and formaldehyde | 0.20 |
| 10 | Sodium lauroylsarcosinate | 0.10 | Polyethylene glycol(15) octylphenyl ether | 0.15 |
| 11 | Sodium lauroylsarcosinate | 0.30 | Polyglycerin(7) monolaurate | 0.20 |
| 12 | Sodium lauroylsarcosinate | 0.15 | Polyethylene glycol(30)-polypropylene glycol(6) decyltetradecyl ether | 0.25 |
| 13 | Sodium polyethylene glycol(4) lauryl ether sulfate | 0.17 | Polyethylene glycol(15) octylphenyl ether | 0.08 |
| 14 | Sodium polyethylene glycol(4) lauryl ether sulfate | 0.15 | Polyethylene glycol(15) stearate | 0.10 |
| 15 | Sodium polyethylene glycol(4) lauryl ether sulfate | 0.25 | Condensate of polyethylene glycol(30) nonylphenyl ether and formaldehyde | 0.05 |
| 16 | Sodium polyethylene glycol(10) lauryl ether phosphate | 0.40 | Tri(polyethylene glycol(10) alkyl ether) phosphate | 0.60 |
| 17 | Sodium polyethylene glycol(10) alkyl ether phosphate | 0.30 | Polyethylene glycol(15) octylphenyl ether | 0.20 |
| 18 | Sodium α-olefin sulfonate | 0.50 | Polyoxyethylene(20) sorbitan monolaurate | 0.75 |

The obtained aqueous solutions were subjected to the following tests.

(1) Cleaning test

There were employed as specimens 270 pieces of commercially available water-nonabsorptive contact lenses (commercial name "MENICON $O_2$" made by Toyo Contact Lens Co., Ltd.), and the haze ($h_0$%) of each specimen was previously measured according to JIS K 6714 by employing a hazeometer (commercial name "Tarbidity Meter T-2500" made by Tokyo Denshoku Kabushiki Kaisha).

An artificial contaminant consisting of the following components were prepared, and it was completely fixed to the lens surface to give compulsory contaminated specimens by uniformly applying it to the lens surface and drying for 8 hours in vacuo.

| Component | Part by weight |
|---|---|
| Tripalmitin | 1.50 |
| Cetanol | 0.50 |
| Palmitic acid | 1.00 |
| Oleic acid | 1.00 |
| Linolic acid | 1.00 |
| SPERMACETI*[1] | 1.50 |
| Cholesterol | 0.50 |
| Cholesterol palmitate | 0.50 |
| Lecithin | 0.75 |

(Note)
*[1]Commercial name of a higher alcohol ester of a higher fatty acid containing as a main component cetyl myristate, made by Nippon Oil and Fats Co., Ltd.

Five 1.5 ml. portions of each of the aqueous solutions obtained in Run Nos. 1 to 18 and the comparative aqueous solutions were placed in contact lens storage containers (commercial name "MENICASE" made by Toyo Contact Lens Co., Ltd.). One contaminated specimen was soaked in the aqueous solution in each container, and allowed to stand for a prescribed period of time.

After soaking for 0.5 or 1.5 hours, the specimens were taken out from the containers, rinsed with a running water for 10 seconds and dried in vacuo. The haze ($h_1$%) of the cleaned specimens was measured by a hazeometer in the same manner as above. The remaining contaminant on the lens surface was evaluated on the basis of the value obtained by subtracting the haze value $h_0$ of the artificially uncontaminated specimen from the haze value $h_1$. The smaller the ($h_1 - h_0$) value, the larger the cleaning effect.

The results are shown in Table 2 where the average ($h_1 - h_0$) value of the five specimens is indicated.

TABLE 2

| Run No. | Soaking time (hour) | Aqueous solution containing anionic and non-ionic surface active agents (%) | Aqueous solution containing only anionic surface active agent (%) | Aqueous solution containing only non-ionic surface active agent (%) |
|---|---|---|---|---|
| 1 | 0.5 | 0.57 | 0.72 | 1.23 |
| 2 | 0.5 | 0.70 | 0.81 | 3.25 |
| 3 | 0.5 | 0.01 | 0.13 | test being impossible due to insoluble |
| 4 | 0.5 | 0.37 | 0.87 | 3.51 |
| 5 | 0.5 | 0.31 | 0.54 | test being impossible due to insoluble |
| 6 | 0.5 | 0.45 | 0.59 | test being impossible due to insoluble |
| 7 | 0.5 | 0.00 | 0.21 | test being impossible due to insoluble |
| 8 | 0.5 | 0.00 | 0.03 | test being impossible due to insoluble |
| 9 | 1.5 | 0.05 | 0.20 | 0.31 |
| 10 | 1.5 | 0.47 | 1.27 | 0.70 |
| 11 | 1.5 | 0.59 | 1.26 | 2.72 |
| 12 | 1.5 | 0.87 | 1.17 | 2.49 |
| 13 | 1.5 | 0.08 | 0.23 | 0.37 |
| 14 | 1.5 | 0.33 | 0.51 | 3.57 |
| 15 | 1.5 | 0.04 | 0.48 | 2.14 |
| 16 | 1.5 | 1.73 | 14.00 | 3.25 |
| 17 | 1.5 | 0.10 | 32.90 | 0.25 |
| 18 | 0.5 | 0.47 | 0.81 | 1.54 |

It is observed in Table 2 that all aqueous solutions according to the present invention using a combination of anionic and non-ionic surface active agents have a marked cleaning effect as compared with the comparative aqueous solutions containing only either anionic or non-ionic surface active agent.

In this Example, the cleaning effect is evaluated with respect to cleaning by only soaking in an aqueous solution. When a contaminated contact lens is rinsed with an aqueous cleaning and storage solution, while applying the aqueous solution to the lens and rubbing with fingers, a more remarkable cleaning effect is obtained.

(2) Safety test

To one eye of a group of 3 albino rabbits was instilled 0.1 ml. of each of the aqueous solutions according to the invention and the comparative aqueous solutions obtained in Run Nos. 1 to 18. The other eye for blank was instilled 0.1 ml. of a physiological saline solution.

After 30 minutes from the instillation, anterior eyes were examined. In the examination, conjunctival injection, injection of the iris, sebum and corneal opacity were observed by the naked eye, and erosio corneae was observed by a slit lamp. The results of the above observations were synthetically judged, and the safety was estimated in five grade. Symbol "−" shows the highest safety, and the safety decreases in the order of "−", "±", "+", "++" and "+++".

The results are shown in Table 3.

TABLE 3

| Run. No. | Aqueous solution containing anionic and non-ionic surface active agents | | | Aqueous solution containing only anionic surface active agent | | | Aqueous solution containing only non-ionic surface active agent | | |
|---|---|---|---|---|---|---|---|---|---|
| 1 | + | + | + | + | ++ | ++ | + | + | ++ |
| 2 | ± | + | + | + | ++ | ++ | + | + | + |
| 3 | + | ++ | ++ | ++ | ++ | ++ | + | + | + |
| 4 | + | + | + | + | + | ++ | + | + | + |
| 5 | + | + | ++ | ++ | ++ | ++ | test being impossible due to insoluble | | |
| 6 | + | + | ++ | + | ++ | ++ | test being impossible due to insoluble | | |
| 7 | + | ++ | ++ | ++ | ++ | ++ | + | + | + |
| 8 | + | + | ++ | ++ | ++ | ++ | test being impossible due to insoluble | | |
| 9 | − | − | − | + | + | + | − | − | + |
| 10 | − | − | ± | + | + | + | ± | + | + |
| 11 | − | − | + | + | + | ++ | + | + | + |
| 12 | − | − | ± | + | + | + | ± | + | + |
| 13 | − | − | − | − | − | + | + | + | + |
| 14 | − | − | − | − | − | ± | ± | + | + |
| 15 | − | − | + | − | + | + | − | − | ± |
| 16 | − | ± | + | + | + | ++ | + | + | + |
| 17 | ± | ± | + | + | + | + | + | + | ++ |
| 18 | + | + | + | + | + | ++ | ± | ± | + |

From the results shown in Table 3, it is understood that the aqueous solutions of the invention using a combination of anionic and non-ionic surface active agents have an equal or less influence upon cornea as compared with a single use of an anionic or non-ionic surface active agent and have a high safety.

EXAMPLES 2 TO 7

There were prepared various kinds of aqueous cleaning and storage solutions having the composition shown in Table 4 where the contents of the respective components in the aqueous solutions were represented by w/v%.

TABLE 4

| Components (w/v %) | Ex. 2 | Ex. 3 | Ex. 4 | Ex. 5 | Ex. 6 | Ex. 7 |
|---|---|---|---|---|---|---|
| Anionic surface active agent | | | | | | |
| Sodium dodecylbenzene sulfonate | 0.125 | — | — | — | — | — |
| Sodium lauryl sulfate | — | 0.30 | — | — | — | — |
| Sodium lauroylmethyltaurate | — | — | 0.10 | — | — | — |
| Sodium α-olefin sulfonate | — | — | — | 0.50 | — | 1.15 |
| Sodium laurylbenzene sulfonate | — | — | — | — | 1.0 | — |
| Non-ionic surface active agent | | | | | | |
| Polyethylene glycol(15) octylphenyl ether | 0.125 | — | — | — | — | — |
| Polyglycerin(7) monolaurate | — | 0.20 | — | — | — | — |
| Condensate of polyethylene glycol(30) nonylphenyl ether and formaldehyde | — | — | 0.20 | — | — | — |
| Polyoxyethylene(20) sorbitan monolaurate | — | — | — | 0.75 | — | — |
| Lauryl diethanolamide | — | — | — | — | 2.1 | — |
| Polyethylene glycol(9) sec-alkyl ether* | — | — | — | — | — | 0.7 |
| Sodium alginate | 0.50 | — | 0.20 | — | — | — |
| Sodium carboxymethyl cellulose | — | 0.30 | 0.30 | 0.50 | — | — |
| Hydroxyethyl cellulose | — | — | — | — | — | 0.35 |
| Trisodium citrate | 1.76 | — | 2.43 | 1.76 | — | — |
| Sodium malate | — | 1.50 | — | — | — | — |
| Bronopol | 0.001 | 0.001 | 0.001 | 0.001 | 0.01 | 0.01 |
| Thimerosal | — | — | — | 0.001 | 0.004 | — |
| Ethylenediaminetetraacetic acid | 0.02 | 0.02 | 0.01 | 0.05 | 0.10 | 0.05 |
| Sodium chloride | 0.25 | 0.33 | — | 0.25 | 0.90 | — |

(Note)
*Commercial name "Softanol 90" made by Nippon Shokubai Kagaku Kogyo Co., Ltd.

The obtained contact lens cleaning and storage solutions were subjected to the cleaning test and safety test in the same manner as in Example 1, and it was confirmed that they had an excellent cleaning effect and has a high safety.

In addition to the components used in the Examples, other components can be used in the Examples as set forth in the specification to obtain substantially the same results.

What we claim is:

1. An aqueous water-nonabsorptive contact lens cleaning and storage solution consisting essentially of (1) an anionic surface active agent, (2) a non-ionic surface active agent, and (3) a compound selected from the group consisting of polysaccharides and derivatives thereof, the ratio of the component (1) to the component (2) being from about 32:68 to about 94:6 by weight, the total concentration of the components (1) and (2) being from about 0.05 to about 4.5% by weight, the concentration of the component (3) being from 0.01 to 10% by weight, and said solution having a pH of 4.8 to 8.5,
    wherein the anionic surface active agent is selected from the group consisting of a sodium alkylbenzene sulfonate, a sodium alpha-olefin sulfonate, a sodium polyoxyethylene alkylether sulfates, a sodium alkyloylmethyltaurinate, a sodium alkyloylsarcosinate, a sodium polyoxyethylene alkylether phosphate, a sodium di(polyexythylene alkylether)phosphate, and a sodium polyoxyethylene alkylphenylether sulfate; and
    wherein the non-ionic surface active agent is selected from the group consisting of a polyoxyethylene higher fatty acid ester, a higher fatty acid ester with a polyoxyalkylene-polyoxyethylene copolymer; a higher fatty acid ester with a polyhydric alcohol; a higher fatty acid ester with a polyoxyethylene polyhydric alcohol including polyoxyethylene glyceryl fatty acid esters and polyoxyethylene sorbitan fatty acid esters; a polyglycerin fatty acid ester; a polyoxyethylene alkyl ether; a polyglycerin ether with an alcohol; a polyoxyethylene fatty acid amide; a polyoxyethylene alkylamine; a polyoxyethylene alkylphenyl ether; a condensate of polyoxyethylene alkylphenol ether with formaldehyde; a polyoxyethylenepolyoxypropylene block copolymer; a phosphate, a polyethyleneglycol adduct of one of a hydrogenated castor oil, castor oil and sterol; and a polyoxyethylene sorbian fatty acid ester.

2. The solution of claim 1, wherein said anionic surface active agent is a member selected from the group consisting of a sodium alkylbenzene sulfonate, a sodium α-olefin sulfonate, a sodium polyoxyethylene alkylether sulfate and a sodium polyoxyethylene alkylphenylether sulfate.

3. The solution of claim 1, wherein said non-ionic surface active agent is a member selected from the group consisting of a polyglycerin fatty acid ester, a polyoxyethylene fatty acid ester, a polyoxyethylene alkyl ether and a polyoxyethylene alkylphenyl ether.

4. An aqueous water-nonabsorptive contact lens cleaning and storage solution consisting essentially of (1) an anionic surface active agent, (2) a non-ionic surface active agent, and (3) a compound selected from the group consisting of polysaccharides and derivatives thereof, the ratio of the component (1) to the component (2) being from about 32:68 to about 94:6 by weight, the total concentration of the components (1) and (2) being from about 0.05 to about 4.5% by weight, the concentration of the component (3) being from about 0.1 to 10% by weight, and said solution having a pH of 4.8 to 8.5,
    wherein said anionic surface active agent is a member selected from the group consisting of sodium alkylbenzene sulfonate, a sodium α-olefin sulfonate, a sodium polyoxyethylene alkylether sulfate and a sodium polyoxyethylene alkylphenylether sulfate, and said non-ionic surface active agent is a member selected from the group consisting from the group consisting of a polyglycerin fatty acid ester, a polyoxyethylene fatty acid ester, a polyoxyethylene alkyl ether and a polyoxyethylene alkylphenyl ether.

* * * * *